United States Patent [19]

Hermele

[11] Patent Number: 5,202,362
[45] Date of Patent: Apr. 13, 1993

[54] SYRINGEABLE EAR PLUG MOLDING PUTTY COMPOSITION

[75] Inventor: Jules J. Hermele, Farmingville, N.Y.

[73] Assignee: Intech Specialties Co., Inc., N. Massapequa, N.Y.

[21] Appl. No.: 756,894

[22] Filed: Sep. 9, 1991

[51] Int. Cl.$^5$ .............................................. C08J 9/32
[52] U.S. Cl. .................................... 523/218; 523/105; 521/54; 521/58; 524/588; 128/867
[58] Field of Search ................. 523/105, 218; 524/588; 521/58, 54; 128/867

[56] References Cited

U.S. PATENT DOCUMENTS

| | | | |
|---|---|---|---|
| 4,528,303 | 7/1985 | Segaud | 524/588 |
| 4,540,063 | 9/1985 | Ochi | 128/867 |
| 4,722,943 | 2/1988 | Melber | 521/58 |
| 4,849,456 | 7/1989 | Champion | 521/54 |
| 4,867,968 | 9/1989 | Allen | 523/105 |

Primary Examiner—Thurman K. Page
Assistant Examiner—William E. Benston

[57] ABSTRACT

A lightweight silicone ear molding putty composition is disclosed for chronic ear patients and myringotomy children to protect ears which includes a mixture comprising of silicone hydroxy functional fluid, crosslinker, and tints as well as a number of additives for adjusting the properties of the mixture and further including an admixture of hollow thermoplastic microspheres containing microcrystalline silica embedded onto the sphere combined with a 5 micron diatomic functional filler. The final composition cures in five minutes to a floating ear plug. Utilizing a mixture of thermoplastic microspheres of 10 to 80 microns and silicone hydroxy fluid ranging from 18,000 to 20,000 centipoise said composition is cured at room temperature, hand mixed, moldable, and syringed into the ear to make an ear plug or mold which has superior properties over prior art ear plugs.

9 Claims, 3 Drawing Sheets

SYRINGEABLE EAR PLUG MOLDING PUTTY COMPOSITION

TECHNICAL FIELD

This invention relates to silicone compositions and more particularly to lightweight moldable plugs made for chronic ear patients and myringotomy children.

BACKGROUND OF THE INVENTION

Audiologists generally utilize the application of a molding composition used to make impressions of ear canals which are sent to laboratories for the purpose of duplicating and creating an ear plug. These ear plugs are made from various materials which are then hollowed out and sealed to prevent water intrusion. This practice is very common but delays exist between when the patient receives the plug and when the impression is taken. Usually requiring a week or more for the patient to return to be fitted with the final ear plug.

Some molding material is used which is molded in the office and is considered the final ear plug. These plugs do not float, are heavy and sink when put in water. Should they be dropped or come loose from the ear in water, such as a pool or the beach, they sink which makes them difficult to find and easy to lose.

Generally, silicone impression material is used for this application as it is considered non-toxic and gives very good reproduction of the impression.

As a binder in these compositions silicone reactive fluid is employed which is mixed with various fillers such as calcium carbonates, silica, and clays to create a putty-like composition which is syringed or hand packed into the ear canal. This material cures in a short amount of time and is removed and sealed with a glaze. The final product varies in hardness, has a specific gravity greater than one and sinks when immersed in water.

In U.S. Pat. No. 4,849,456 to Champion, a casting composition for marble products is disclosed for shaped bathroom products which contains ceramic spheres and plastic spheres. The compound includes an average diameter of plastic spheres significantly less than the diameter of ceramic spheres. The hollow spheres are said to produce a lighter weight composition and the plastic spheres are present in the composition to cushion the ceramic spheres during handling, mixing, and casting of the filler composition. The plastic spheres having a diameter of 3 to 5 microns and the ceramic spheres having a diameter of 10 to 300 microns.

In U.S. Pat. No. 4,528,303 to Segaud et al, a polymer/filler molding composition consisting of a polymeric matrix, an inorganic reinforcing filler and a coupling agent consisting of enstatite and silica prepared by the calcination of a precursor clay. The compositions may contain calcium carbonates, titanium dioxide, silica, aluminosilicate, talc, wollastonite, and calcium sulfate as reinforcing fillers. The said elastomeric silicone compositions are intended to be made from products obtained by crosslinking, under the action of heat.

Although various types of fillers are disclosed for inclusion in base compositions for molding, the final compositions are typically of substantial weight and do not achieve optimum application characteristics, particularly where hand mix and syringing are required. Consequently, the search continues for ear molding compositions which include fillers which reduce weight and may be floatable in water.

SUMMARY OF THE INVENTION

It is the object of the present invention to provide an instant floating silicone composition which cures at room temperature.

It is another object of the present invention to provide a composition which can be hand packed or syringeable.

It is another object of the present invention to provide a mixture which can be hand mixed with the fingers in the hand without sticking and remaining putty-like.

It is another object of the present invention to provide a surface which makes a detailed impression of the ear canal.

It is another object of the present invention to maintain a durable, elastic, and flexible material which resists the constant insertion and removal from the ear.

It is yet another object of the invention to maintain a long and stable shelf life with minimal change in viscosity characteristics.

According to the present invention, a lightweight and syringeahle composition is disclosed which comprises a silicone based formulation which may include various fillers and additives for adjusting the composition such as crosslinkers, or pigments. The composition further includes an admixture of thermoplastic microspheres which have a microcrystalline silica treated surface. The surface of the sphere has been treated with microcrystalline silica which is embedded into the surface of the sphere during its manufacture.

Utilizing an admixture of 18,000 to 20,000 centipoise viscosity dimethyl silicone reactive fluid with 10 to 80 micron surface treated thermoplastic microspheres, and 5 micron diatomaceous functional filler provides a mixture which can be hand mixed without sticking to the skin or fingers and can be molded by hand. The final cured composition is instant floating and can be used immediately.

Another advantage to the composition is the flexibility of the impression. The elastic nature of the thermoplastic spheres allows increased deformation capability while integrally bonding to the silicone via the microsilica attached to its surface. The chemical and mechanical bonding provides durability and greater strength.

DETAILED DESCRIPTION OF THE INVENTION

The composition of the present invention includes a base composition which may comprise a mixture of dimethyl silicone reactive fluid, condensed ethyl silicate crosslinker, organic pigment for color, and an odor mask. Generally the base composition are well known in the art for producing silicone compounds. While a particular combination of components will be discussed, it will be understood by those skilled in the art that various combinations of materials, ingredients, and additives can be used to produce a base composition.

For producing an instant floating, hand mix, syringeable putty compound, a key property is the viscosity and degree of tackiness. Generally, viscosities greater than 1 million centipoise are common, with such viscosities achieved by the controlled addition of fillers.

Figure 2:
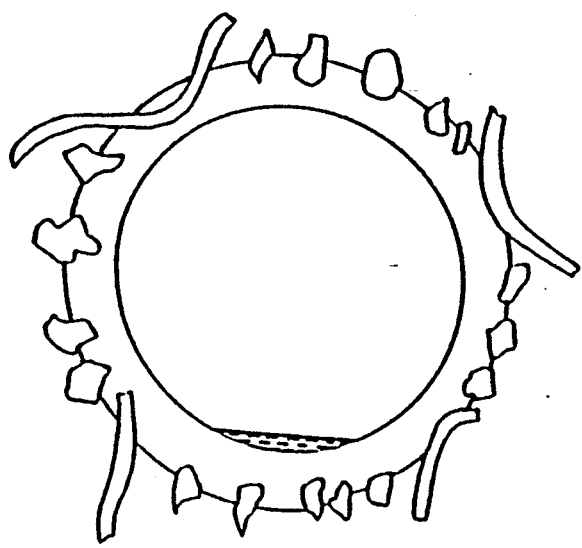
FIG. 2 shows a representative microscopic view of a composition of silica treated thermoplastic microsphere.
Figure 3:
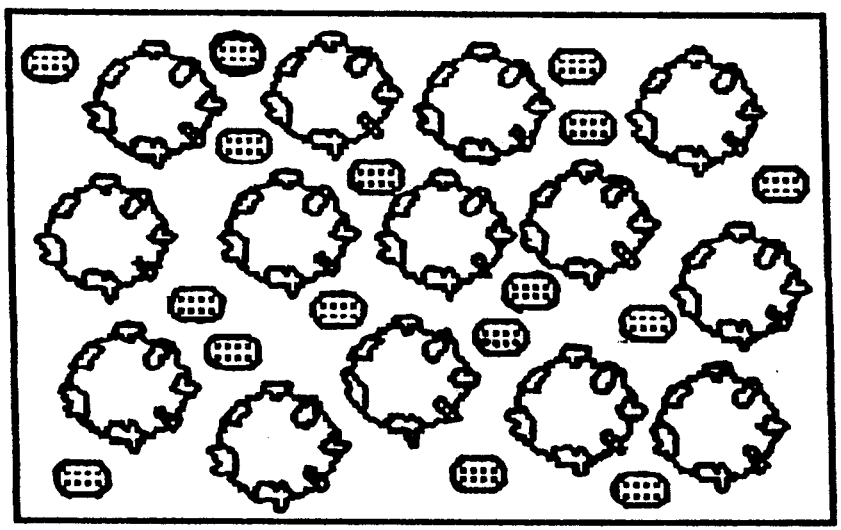
FIG. 3 shows a representative microscopic view of a composition of the invention.

The inventive composition includes an admixture of microcrystalline silica treated thermoplastic microspheres in which the silica has been bonded to the surface during the formation of the microsphere. FIG. 2 shows a microscopic view of the silica treated thermoplastic microsphere.

The microspheres a density of 0.25 to 0.44 with the surface treatment. The structure of the microsphere is that as disclosed in U.S. Pat. No. 4,722,943 to Melber et al. Generally microspheres made from hollow glass or ceramic are unacceptable as they are easily broken under shear when making high viscosity mixtures and contain trace metals, are alkaline in nature and are unstable in silicone compositions. High viscosity and hard shear are possible using thermoplastic microspheres as they are less sensitive to shear and will not break. The microspheres have a diameter from 10 to 80 microns with 80 microns being preferred. The combination of 18,000 to 20,000 centipoise silicone reactive fluid and diatomaceous functional filler with a median particle size of 5 microns allow a composition which has a specific gravity less than one while maintaining structural integrity and non-sticky putty characteristics.

Figure 1:
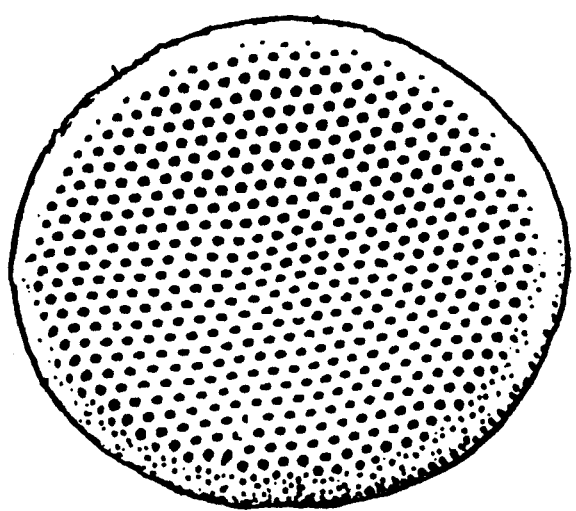
FIG. 1 shows a representative microscopic view of a composition of diatomic filler.

The use of diatomaceous functional filler with surface treated thermoplastic microspheres provides unique properties associated with the diatomic structure. FIG. 1 shows a microscopic view of the diatomic structure. Diatomic structure results from the skeletal remains of single-cell aquatic plants called diatoms. This structure contains lacework patterns of great variety and complexity. Since the total thickness of the cell wall is only a few ten thousandths of an inch, the internal structure is highly porous on a microscopic scale. The skeletal remains become an inorganic mineral containing a diatomic structure.

Utilizing surface treated thermoplastic microspheres and diatomic filler according to the invention provides enhanced physical properties of the cured composition.

A typical formulation including the microsphere and diatomaceous functional filler is disclosed in Table 1.

Utilizing thermoplastic microspheres with diatomaceous functional filler provide a very low content of heavy metals which prevents the negative effect of catalyzing the composition during storage. The composition in Table 1 has excellent shelf life compared to glass, ceramic microspheres or other naturally occurring fillers.

Also the specific gravity of the diatomaceous functional filler is lower than conventional fillers due to its internal structure and provides balanced loading while helping to maintain a specific gravity of the overall composition less than one. The optimum level of diatomaceous functional filler is in the range of 6–8 percent. Levels outside this range result in stickiness or tackiness while kneading with the fingers and reduced physical properties when cured.

The overall particle size is very important to obtain good molding reproduction for proper fitting swim plugs. Increasing particle size of the spheres or diatomic fillers cause increased stickiness and tack during forming and lower viscosities.

TABLE 1

| Ingredients | Wt. |
| --- | --- |
| PART A | |
| Silicone Reactive Fluid 18,000 cps | 64.7 |
| Ethyl Silicate | 4.4 |
| Thermoplastic Microsphere 80 micron | 22.0 |
| Diatomaceous Functional Filler 5 micron | 7.0 |
| Phthalo Blue or Red tint | 1.1 |
| Fragrance odor mask | 0.3 |
| PART B | |
| Catalyst | 0.5 |
| Stannous Octoate | |

Another advantage of the cured composition is its lightweight nature which is less noticeable when wearing in the ear. Being light, it is less fatiguing or discomforting to wear. Since it floats it is less likely to be lost as it can float to the surface. Its detailed impression of the ear canal and flexibility provide a tight fit which flexes with the jaw bone movement and prevents water intrusion in myringotomy patients.

The inventive composition is manufactured using conventional putty or paste type mixers. To produce the composition of Table 1, the silicone reactive fluid is first charged to the mixing tank which may be made of mild steel or stainless steel. The other ingredients such as Ethyl Silicate, tint, and odor mask, are then added and dispersed well. The addition of thermoplastic microspheres is then mixed into the composition untill a soft paste is attained. Finally the diatomaceous filler is added until the final putty is attained. Overshearing is of little concern as the microspheres do not fracture. Where it is desired to make different colors, various colors of tints can be added provided they are low in heavy metal content which may affect the storage and shelf life of the composition.

While this invention discussed in relation to an impression material including a plurality of additives included therein, it will be understood by those skilled in the art that any changes in the choice or quantity of the base composition can be made without varying from the scope of the present invention.

I claim:

1. A syringeable ear plug molding putty composition suitable for room temperature application and curing, having a viscosity of 1 million centipoise, and used for creating instant floating ear plugs,
   the base composition thereof including a silicone reactive fluid with additives dispersed therein, and the putty composition further comprising:
   an admixture of surface treated thermoplastic microspheres and a diatomaceous functional filter, the microsphere to diatomaceous filler having a ratio of 3 to 1 by weight, the admixture comprising 25 to 35 percent by weight of the putty composition.

2. The composition of matter as defined by claim 1, said thermoplastic microspheres having a diameter of 10 to 80 microns, and having a surface treatment of embedded and/or adhered to their surface; microcrystalline silica.

3. The composition of matter as defined by claim 1, said distomaceous functional filler having a mean particle size of 5 microns and having a diatomical structure.

4. The composition of matter as defined by claim 1 wherein the base composition includes additives consisting of Ethyl Silicate, Tints, and a Fragrance.

5. The molding putty composition as defined by claim 1 is activated and sets in 5 to 10 minutes at room temperature by the addition of a catalyst consisting of Stannous Octoate during hand mixing prior to syringing into the ear.

6. The molding putty composition as defined by claim 1 can be hand packed or syringed into the ear.

7. The molding putty composition as defined by claim 1 can be hand mixed and cures at room temperature without sticking to the fingers or hands.

8. The molding putty composition as defined by claim 1 is instant floating, has a specific gravity less than one, and has a minimum shelf life of one year.

9. The molding putty composition as defined by claim 1 is soft, flexible and provides a detailed impression of the ear canal to prevent water intrusion in chronic ear patients and myringotomy children.

* * * * *